(12) United States Patent
Strohmaier

(10) Patent No.: US 6,835,363 B1
(45) Date of Patent: Dec. 28, 2004

(54) SYNTHESIS OF MOLECULAR SIEVES OF CHA FRAMEWORK TYPE

(75) Inventor: Karl G. Strohmaier, Port Murray, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/635,173

(22) Filed: Aug. 6, 2003

(51) Int. Cl.$^7$ .......................... C01B 37/04; C01B 37/08; B01J 29/83; B01J 29/85
(52) U.S. Cl. ............... 423/305; 423/306; 423/DIG. 30; 502/208; 502/214; 208/46
(58) Field of Search ............................... 423/305, 306, 423/DIG. 30; 502/208, 214; 208/46

(56) References Cited

U.S. PATENT DOCUMENTS

| | | | |
|---|---|---|---|
| 4,310,440 A | 1/1982 | Wilson et al. | 252/435 |
| 4,440,871 A | 4/1984 | Lok et al. | 502/214 |
| 4,801,743 A | 1/1989 | Baugh et al. | 562/519 |
| 4,861,739 A | 8/1989 | Pellet et al. | 502/64 |
| 4,898,660 A | 2/1990 | Wilson et al. | 208/114 |
| 5,096,684 A | 3/1992 | Guth et al. | 423/306 |
| 5,232,683 A | 8/1993 | Clark et al. | 423/708 |
| 5,370,851 A | 12/1994 | Wilson | 423/305 |
| 5,514,362 A | 5/1996 | Miller | 423/702 |
| 5,879,655 A | 3/1999 | Miller et al. | 423/702 |
| 6,162,415 A | 12/2000 | Liu et al. | 423/706 |
| 6,540,970 B1 * | 4/2003 | Strohmaier et al. | 423/306 |
| 6,620,983 B1 * | 9/2003 | Cao et al. | 585/640 |
| 6,680,278 B2 * | 1/2004 | Cao et al. | 502/214 |
| 2003/0231999 A1 * | 12/2003 | Cao et al. | 423/305 |

FOREIGN PATENT DOCUMENTS

| | | | |
|---|---|---|---|
| CN | 1299776 | 12/1999 | C01B/37/08 |
| CN | 1301598 | 12/1999 | B01J/29/85 |
| EP | 0 043 562 | 6/1984 | C01B/25/36 |
| EP | 0 538 958 | 4/1993 | C01B/25/36 |
| EP | 0 993 867 | 4/2000 | B01J/29/85 |
| EP | 1 142 833 | 10/2001 | C01B/37/06 |

OTHER PUBLICATIONS

"Atlas of Zeolite Framework Types", 5$^{th}$ Edition, p. 96 (2001).
Feng et al., Microporous and Mesoporous Materials, vol. 23, No. 3–4, pp. 221–229 (1998).
Wilson et al., Microporous and Mesoporous Materials, vol. 18, No. 1, pp. 125–137 (1999).
Wilson et al., Studies in Surface Science and Catalysis, vol. 98, pp. 9–10 (1995).
Bu et al., Microporous and Mesoporous Materials, vol. 25, No. 1–3, pp. 109–117, (1998).
Feng et al., Nature (London), vol. 388, pp. 735–741.
Ferey et al., Journal of Solid State Chemistry, vol. 105 (1), pp. 179–190 (1993).
Long et al., Chemical Journal of Chinese Universities, vol. 7(2), pp. 100–104 (1986).
Long et al., Journal of Fudan University (Natural Science) vol. 25(3) pp. 301–308, (1986).
Tian, et al., Studies in Surface Science and Catalysis 135 (Zeolites and Mesoporous Materials at the Dawn of the 21st Century), pp. 891–898 (2001).
Tian et al., Chemical Journal of Chinese Universities, vol. 22(6), pp. 991–994 (2001).
Kessler, H., et al., "The opportunities of the fluoride route in the synthesis of microporous materials", Studies in Surface Science and Applications, vol. 85, 1994, pp. 75–113, Elsevier Science B.V.

* cited by examiner

Primary Examiner—David Sample

(57) ABSTRACT

The invention is directed to a method of synthesizing aluminophosphate and silicoaluminophosphate molecular sieves and in particular to the synthesis of aluminophosphate and silicoaluminophosphate molecular sieves using the synthesis templates that contain two dimethylamino moieties in combination with hydrogen fluoride. The use of this template in combination with hydrogen fluoride results in good quality SAPO molecular sieves of CHA framework type with low levels of silicon that are produced in relatively short crystallization times.

47 Claims, No Drawings

SYNTHESIS OF MOLECULAR SIEVES OF CHA FRAMEWORK TYPE

FIELD OF INVENTION

This invention relates to the synthesis of aluminophosphate and silicoaluminophosphate molecular sieves of the CHA framework type. In particular the present invention relates to the synthesis of aluminophosphate and silicoaluminophosphate molecular sieves of the CHA framework type using synthesis templates that contain two dimethylamino moieties in combination with hydrogen fluoride.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. It has been known for some time that oxygenates, especially alcohols, e.g. methanol, are convertible into light olefin(s). The preferred methanol conversion process is generally referred to as methanol-to-olefin(s) (MTO) process, where methanol is converted to primarily ethylene and propylene in the presence of a molecular sieve.

Some of the most useful molecular sieves for converting methanol to olefin(s) are the metalloalluminophosphates such as the silicoaluminophosphates (SAPO's). There are a wide variety of SAPO molecular sieves known in the art, of these the more important examples include SAPO-5, SAPO-11, SAPO-18, SAPO-34, SAPO-35, SAPO-41, and SAPO-56. For the methanol-to-olefins process SAPO molecular sieves having the CHA framework type ("Atlas of Zeolite Framework Types", 2001, 5th Edition, p. 96) and especially SAPO-34 are particularly important catalysts. The CHA framework type has a double six-ring structure in an ABC stacking arrangement. The pore openings of the structure are defined by eight member rings that have a diameter of about 4.0 Å, and cylindrical cages within the structure of approximately 10×6.7 Å. Other SAPO molecular sieves of CHA framework type include SAPO-44, SAPO-47 and ZYT-6.

The synthesis of $AlPO_4$ and SAPO molecular sieves is a complicated process. There are a number of variables, which need to be controlled in order to optimise the synthesis in terms of the purity, yield, and quality of the molecular sieve produced. Of these variables the choice of synthesis template is usually one of the most important in determining which framework type is obtained.

One desirable group of silicoaluminophosphate molecular sieves are those, which have low silicon contents. Silicoaluminophosphates of the CHA framework type with low silicon contents are particularly desirable for use in the methanol-to-olefins process. Wilson, et al., reported that it is beneficial to have lower Si content for methanol-to-olefins reaction (*Microporous and Mesoporous Materials*, 29, 117–126, 1999). Low Si content has the effect of reducing propane formation and decreasing catalyst deactivation.

In U.S. Pat. No. 4,440,871 (Lok et al.) the synthesis of a wide variety of SAPO materials of various framework types are described with a number of specific examples. Also disclosed are a large number of possible organic templates, with some specific examples. In the specific examples a number of CHA framework type materials are described. SAPO-34 is prepared utilising tetraethylammonium hydroxide (TEAOH), or isopropylamine, or mixtures of TEAOH and dipropylamine (DPA). This is believed to be the first reported synthesis of a SAPO-34 of CHA framework type. Also disclosed in this patent is a specific example that utilises cyclohexylamine in the preparation of SAPO-44. Although other template materials are described in this patent there are no other templates indicated as being suitable for preparing SAPO's of CHA framework type. Certain aminoalcohols are mentioned, including triethanolamine, N-methyldiethanolamine, N-methylethanolamine, N,N-dimethylethanolamine and N,N-diethylethanolamine as possible templates for SAPO molecular sieves. Of these materials N,N-diethylethanolamine is shown to produce SAPO-5, which is of framework type AFI. For the other aminoalcohols no indication is provided as to which SAPO or which framework type may be obtained through their use.

Since the synthesis of SAPO-34 was reported in U.S. Pat. No. 4,440,871, tetraethylammonium hydroxide (TEAOH) either alone, or in combination with dipropyl amine (DPA), has been the template of choice for preparing SAPO-34. However, there are problems associated with the use of TEAOH and DPA. When used alone, TEAOH affords a limited range of synthesis parameters. For example, under certain conditions TEAOH will also template the synthesis of SAPO-18, which has the AEI framework type. TEAOH is thus relatively intolerant to synthesis condition variations. TEAOH is sometimes combined with DPA. However, DPA has a low boiling point (110° C.) resulting in the need for production plants that can handle high pressures. In certain countries, the use of DPA requires special regulatory authorizations due to its toxicity. Also, DPA is an aggressive template and is often implicated in re-dissolution of the silicoaluminophosphate molecular sieve during its synthesis, resulting in poor quality crystalline product due to surface pitting of the crystals. Finally, it has proved difficult up to now to make pure phase CHA silicoaluminophosphate molecular sieves with low silica to alumina ratio. Although there are problems associated with TEAOH and DPA, no completely satisfactory alternative template materials have been reported yet for the preparation of silicoaluminophosphate molecular sieves with the CHA framework type. A further problem associated with the use of TEAOH is that silicoaluminophosphate molecular sieves with the CHA framework produced using this template are relatively expensive due to long crystallization times that are typically between 24 to 72 hours. In a Ph.D. thesis (E. H. Halvorsen, University of Oslo, 1996), it was reported that low silica SAPO-34, designated as UiO-S4, was produced using TEAOH template in combination with HF. When TEAOH is used in combination with hydrogen fluoride the crystallization times may be reduced to between 16 to 24 hours; whilst this is an improvement the resultant molecular sieves are still expensive.

In U.S. Pat. No. 4,440,871, it was reported that SAPO-44 was obtained "as the major phase" using cyclohexylamine as template. In U.S. Pat. No. 6,162,415 (Liu, et al.), relatively pure CHA SAPO-44 was obtained using the same template but with control of the ratio of template to aluminium component and the ratio of phosphorous component to aluminium component. In European Patent Publication No. 0,993,867, it was reported that the use of methylbutylamine resulted in SAPO-47 and the use of cyclohexylamine resulted in impure SAPO-44. Methylbutylamine has an even lower boiling point, at 91° C., than DPA.

When attempts have been made to utilise other types of template compounds such as aminoalcohols, silicoaluminophosphates of framework type other than CHA have been obtained. In U.S. Pat. No. 4,861,739 (Pellet, et al.), Example 102, it was reported that the use of N,N-diethylethanolamine produced CoAPSO-47, having Si concentrated on the peripheries of the crystal and Co at the centre. In U.S. Pat. No. 4,310,440 (Wilson et al.), triethanolamine, N,N-dimethylethanolamine, N,N-diethylethanolamine, N-methyldiethanolamine, and N-methylethanolamine, were all used to prepare $AlPO_4$-5, aluminophosphates of framework type AFI. N-methylethanolamine was also reported to produce $AlPO_4$-21 of framework type AWO. In European Patent Publication No. 0,993,867, it was reported that diethanolamine produced SAPO-34 and SAPO-5 under different synthesis conditions. To-date all attempts to reproduce this SAPO-34 synthesis have failed.

In the art various attempts have been made to improve the synthesis of $AlPO_4$ or SAPO molecular sieves. One approach has been the use of fluoride addition to the synthesis. In U.S. Pat. No. 5,096,684 (Guth et al.), morpholine and tetraethylammonium hydroxide were found to template the production of SAPO-34 when in the presence of HF. According to Guth et al., the use of HF in combination with the organic template results in silicoaluminophosphates which have improved thermal and hydrolytic stability. No other templates were found to produce silicoaluminophosphates of CHA framework type in the presence of fluoride ions, although various other templates were found to produce many other framework types in the presence of HF. H. Kessler et al. (H. Kessler, J. Patarin and C. Scott-Darie, Studies in Surface Science and Catalysis, Vol. 85 (1994), pp. 75–113) refers to the work of M. Goepper (Ph. D. Thesis of M. Goepper, Université Haute Alsace, Mulhouse (France), 1990). In her thesis, M. Goepper reports crystallization of an aluminophosphate of CHA framework from heating for 24 hours at 200° C. a synthesis mixture having the composition $1.0HF:1.5TMED:Al_2O_3:P_2O_5:80H_2O$. M. Goepper reports that this CHA phase was not obtained when a source of divalent metal was added to the synthesis mixture. In the absence of HF and in the absence of a source of divalent metal, the formation of $AlPO_4$-21 is reported with TMED as template. In U.S. Pat. No. 4,786,487 (Kuehl), SAPO-20 was produced from synthesis mixtures containing tetramethylammonium hydroxide and fluoride ions from water-soluble sources of fluoride such as Na, K and ammonium fluoride. In U.S. Pat. No. 6,001,328 (Lillerud et al.), silicoaluminophosphate indicated as UiO-S7 was prepared using tetramethylammonium hydroxide pentahydrate or tetramethylammonium hydroxide, in combination with HF. In a Ph.D. thesis (E. H. Halvorsen, University of Oslo, 1996), it was reported that low silica SAPO-34, designated as UiO-S4, was produced using TEAOH template in combination with HF.

In the art various attempts have been made to synthesis of $AlPO_4$ or SAPO molecular sieves using templates based on the alkylene diamine or polyamine structures such as for example those based on for example ethylenediamine, 1,3-propanediamine, and 1,6-hexanediamine.

In European Patent Publication No. 0,043,562, it was reported that the use of N,N,N',N'-tetramethyl ethylenediamine as organic template resulted in the formation of $AlPO_4$-21. In European Patent Publication No. 0,538,958, it was reported that the use of N,N,N',N'-tetramethyl ethylenediamine as organic template resulted in the formation of an $AlPO_4$ referred to as SCS-24. In European Patent Publication No. 1,142,833, it was reported that the use of N,N,N',N'-tetramethyl-1,6-hexanediamine as organic template resulted in the formation of MeAPSO-56 and SAPO-56. In U.S. Pat. No. 4,898,660 (Wilson et al.), ethylenediamine was used to prepare $AlPO_4$-12. N,N,N',N'-tetramethyl-propane-1,3-diamine and N,N,N',N'-tetramethyl ethylenediamine were reported to produce $AlPO_4$-21. In U.S. Pat. No. 5,370,851 (Wilson), it was reported that the use of N,N,N',N'-tetramethyl-1,6-hexanediamine as organic template resulted in the formation of SAPO-56. In U.S. Pat. No. 5,232,683 (Clark et al.), it was reported that the use of 1,8-diaminooctane and 1,10-diaminodecane as organic templates resulted in the formation SAPO's and CoAlPO's of type SCS-22. Wilson, et al., have reported the use of N,N,N',N'-tetramethyl-1,6-hexanediamine as organic template resulted in the formation of AlPO-17, SAPO-17, MAPSO-34 and SAPO-56 (*Microporous and Mesoporous Materials*, 28(1), 117–126, 1999 and *Studies in Surface Science and Catalysis* (1995) 98, (*Zeolite Science 1994: Recent Progress and Discussions*), 9–10). Bu, et al., have reported the use of, N,N,N',N'-tetramethyl ethylenediamine and 1,3-diaminopropane as structure directing agents for the formation of cobalt aluminophosphates UCSB-4 and UCSB-5 (*Microporous and Mesoporous Materials*, 25(1–3), 109–117,1998).

Feng, et al., have reported that a variety of cobalt phosphates having zeolite like structures could be prepared using a variety of alkylene diamines as structure directing agents (*Nature (London)*, 388(6644), 735–741,1997). In a latter work it was reported that cobalt aluminophosphates of CHA framework type could be prepared using N,N,N',N'-tetramethyl-1,6-hexanediamine as organic template and a zinc aluminophosphate of CHA framework type could be prepared using N,N,N',N'-tetramethyl-1,3-butanediamine as organic template (*Microporous and Mesoporous Materials*, 23, 221–229,1998). Ferey, et al., have reported that the use of N,N,N',N'-tetramethyl-1,6-hexanediamine as organic template in the presence of ammonium fluoride produced AlPO-CJ2 (*Journal of Solid State Chemistry* 105(1), 179–90, 1993). Long, et al., have reported that the use of N,N,N',N'-tetramethyl ethylenediamine as organic template resulted in the formation of an $AlPO_4$-21 and an $AlPO_4$ molecular sieve named CFAP-2 (*Chemical Journal of Chinese Universities* 7(2), 100–4, 1986 and *Journal of Fudan University (Natural Science)* 25(3), 301–8, 1986). Tian, et al., have reported that the use of N,N,N',N'-tetramethyl-1,6-hexanediamine as organic template resulted in the formation of SAPO-56 and MAPSO-56 molecular sieves (*Studies in Surface Science and Catalysis* (2001), 135 (*Zeolites and Mesoporous Materials at the Dawn of the 21st Century*), 891–898 and *Chemical Journal of Chinese Universities* 22(6), 991–994,2001).

In Chinese Patent No. 1,299,776, it was reported that the use of N,N,N',N'-tetramethyl-1,6-hexanediamine as organic template resulted in the formation of SAPO-56 molecular sieve. In Chinese Patent No. 1,301,598, it was reported that the use of N,N,N',N'-tetramethyl-1,6-hexanediamine as organic template resulted in the formation of SAPO-56, and various MeAPSO-56 molecular sieves.

As can be seen from the disclosures described herein, there have been a number of attempts to find alternative synthesis templates for the CHA framework type with limited success. It is desirable therefore to find new synthesis templates and template systems that are specific for the synthesis of silicoaluminophosphate molecular sieves having the CHA framework type. In addition there is a need for new templating systems which afford more effective control of the final composition of the SAPO molecular sieve materials and in particular the Si content of the final product. In addition a further need is to obtain SAPO materials having the CHA framework type that have a low acid density, which is normally directly related to low silica content. A further desire is to find methods of reducing the crystallization times for the synthesis of aluminophosphate and silicoaluminophosphate.

SUMMARY OF THE INVENTION

The present invention provides a process for preparing microporous crystalline silicoaluminophosphate molecular sieves of CHA framework type, the process comprising:

(a) providing a reaction mixture comprising a source of alumina, a source of phosphate, a source of silica, hydrogen fluoride and an organic template comprising one or more compounds of formula (I):

$$(CH_3)_2N—R—N(CH_3)_2 \qquad (I)$$

wherein R is an alkyl radical of from 1 to 12 carbon atoms;

(b) inducing crystallization of silicoaluminophosphate from the reaction mixture; and (c) recovering silicoaluminophosphate molecular sieve.

In one embodiment of the present invention there is provided a silicoaluminophosphate molecular sieve, substantially of CHA framework type, comprising within its intra-crystalline structure fluoride and at least one template of the formula (I)

$$(CH_3)_2N—R—N(CH_3)_2 \qquad (I)$$

wherein R is an alkyl radical of from 1 to 12 carbon atoms.

In another embodiment, the present invention provides a process for preparing microporous crystalline aluminophosphate molecular sieves of CHA framework type, the process comprising:

(a) providing a reaction mixture comprising a source of alumina, a source of phosphate, hydrogen fluoride and an organic template comprising one or more compounds of formula (I'):

$$(CH_3)_2N—R—N(CH_3)_2 \qquad (I')$$

wherein R is an alkyl radical of from 3 to 12 carbon atoms;

(b) inducing crystallization of aluminophosphate from the reaction mixture; and (c) recovering aluminophosphate molecular sieve.

In another embodiment of the present invention there is provided a composition of a microporous crystalline silicoaluminophosphate molecular sieve, which has a characteristic X-ray powder diffraction pattern containing at least the d-spacings as set forth in Table A:

TABLE A

| d (Å) | I/Io (%) |
|---|---|
| 9.39–9.01 | 80–100 |
| 6.43–6.25 | 5–50 |
| 5.89–5.73 | 5–50 |
| 5.55–5.42 | 20–60 |
| 4.99–4.88 | 20–60 |
| 5.02–4.91 | 5–40 |
| 4.43–4.34 | 5–50 |
| 4.20–4.12 | 30–70 |
| 4.07–4.00 | 30–70 |
| 3.79–3.73 | 5–40 |
| 3.51–3.45 | 5–50 |
| 2.952–2.914 | 5–40 |
| 2.850–2.815 | 5–40 |
| 2.724–2.692 | 20–60 |

It is preferred that the composition as identified in Table A comprises N,N,N',N'-tetramethyl ethylenediamine and fluoride within its intra-crystalline structure.

In another embodiment the present invention provides a method for the manufacture of a formulated catalyst composition, which method comprises forming a mixture comprising at least one microporous crystalline silicoaluminophosphate molecular sieve of CHA framework type comprising within its intra-crystalline structure fluoride and at least one template which contains one or more compounds of general formula (I) wherein R is an alkyl radical of from 1 to 12 carbon atoms or as obtained from a process utilising a template comprising one or more compounds of the formula (I) wherein R is an alkyl radical of from 1 to 12 carbon atoms, in combination with hydrogen fluoride, with at least one formulating agent, to form a catalyst composition.

In yet a further embodiment the present invention provides for a formulated molecular sieve composition comprising at least one microporous crystalline silicoaluminophosphate molecular sieve of CHA framework type comprising within its intra-crystalline structure fluoride and one or more compounds of general formula (I) wherein R is an alkyl radical of from 1 to 12 carbon atoms or as obtained from a process utilising a template comprising one or more compounds of general formula (I) wherein R is an alkyl radical of from 1 to 12 carbon atoms, in combination with hydrogen fluoride, in admixture with at least one formulating agent.

In a further embodiment the present invention provides for the use of a template comprising one or more compounds of general formula (I) wherein R is an alkyl radical of from 1 to 12 carbon atoms in combination with hydrogen fluoride ions in the synthesis of silicoaluminophosphates of CHA framework type.

In yet a further embodiment, the present invention provides for the use of a template comprising one or more compounds of general formula (I') wherein R is an alkyl radical of from 3 to 12 carbon atoms in combination with hydrogen fluoride ions in the synthesis of aluminophosphates of CHA framework type.

DETAILED DESCRIPTION OF THE INVENTION

Introduction

The invention is primarily directed toward a method for synthesising aluminophosphate (AlPO's) and silicoaluminophosphates (SAPO's) of the CHA framework type. Preferably, the method relates to a method for synthesizing silicoaluminophosphates (SAPO's) of the CHA framework type. In particular it has been found that a specific group of organic amines of general formula (I) are effective synthesis templates for SAPO's of the CHA framework type when used in combination with hydrogen fluoride. Also, it has been found that a specific group of amines of genreal formula (I') are effective synthesis templates for ALPOs of the CHA framework type. Through the use of this combination not only is it possible to prepare AlPO's or SAPO's of CHA framework type, when this was not expected, but it is also possible to prepare AlPO's or SAPO's of CHA framework type without also introducing significant impurities of other framework types especially impurities of framework type AWO. Furthermore, it has been found that the use of the specific templates of general formula (I) with hydrogen fluoride in the synthesis affords the production of silicoaluminophosphates of framework type CHA with low silica contents. Also, the use of the specific templates with hydrogen fluoride allows very fast crystallization of silicoaluminophosphates of framework type CHA. These results can be achieved with low concentrations of templates and/or HF.

Although not a preferred embodiment of the present invention it is also possible to utilise this combination of hydrogen fluoride and organic compounds of general formula (I) with other known templates for the synthesis of aluminophosphates or silicoaluminophosphates of CHA framework type in a dual template synthesis. Catalysts containing the molecular sieves obtained by the method of the present invention are particularly useful for methanol-to-olefins conversions.

Silicoaluminophosphates

The AlPO or SAPO molecular sieves of the present invention may be represented by the empirical formula, on an anhydrous basis:

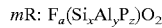

$$mR: F_a(Si_xAl_yP_z)O_2$$

wherein R represents at least one templating agent comprising one or more compounds of general formula (I); m is the number of moles of R per mole of $(Si_xAl_yP_z)O_2$ and m has a value from 0.0417 to 0.3333, preferably 0.0833 to 0.25, and most preferably from 0.0833 to 0.1667; x, y, and z respectively represent the mole fraction of Si, Al and P as tetrahedral oxides. F indicates fluoride ion bound in the precursor material and "a" is the number of moles of F per mole of $(Si_xAl_yP_z)O_2$; a may have a value between 0.001 to 0.167. In relation to AlPO molecular sieves the value of x will be zero.

In an embodiment, m is greater than or equal to 0.05, and x is less than or equal to 0.2, y and z are greater than or equal to 0.01. In another embodiment, m is in the range from greater than 0.01 to about 0.4, x is less than or equal to 0.1, y is in the range of from 0.4 to 0.7, and z is in the range of from 0.25 to 0.9, more preferably m is in the range of from 0.08 to 0.17, x is less than or equal to 0.08, y is in the range of from 0.4 to 0.6, and z is in the range of from 0.3 to 0.5. Preferably, when the molecular sieve is a SAPO, x is greater than or equal to 0.01.

When these materials are calcined the resulting AlPO's or SAPO's have a CHA framework type and are of high purity in terms of their framework type with little or no intergrowth with other silicoaluminophosphate or aluminophosphate framework types and in particular with little or no intergrowth with silicoaluminophosphates or aluminophosphates of AEI framework type. However, prior to calcination the XRD patterns for these materials provides little indication that these materials have the CHA framework type.

Molecular Sieve Synthesis

Generally, alumino- or silicoalumino-phosphate molecular sieves are synthesized by the hydrothermal crystallization of one or more of a source of aluminium, a source of phosphorous, a source of silicon for silicoaluminophosphate, and a templating agent. Typically, in the process of the present invention a combination of sources of silicon, aluminium and phosphorous, optionally with one or more templating agents and/or one or more metal containing compounds and hydrogen fluoride are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a typical synthesis of the molecular sieve, the phosphorous-, aluminium-, and/or silicon-containing components are mixed, preferably while stirring and/or agitation and/or seeding with a crystalline material, optionally with an alkali metal, in a solvent such as water, and one or more templating agents, to form a synthesis mixture. To this synthesis mixture or gel is added the hydrogen fluoride. This mixture or gel is then heated under crystallization conditions of pressure and temperature as described in U.S. Pat. No. 4,440,871, which is fully incorporated by reference.

The templates used in the process of the present invention comprise one or more compounds general formula (I) or (I'):

$$(CH_3)_2N-R-N(CH_3)_2 \qquad (I), (I')$$

wherein R is an alkyl radical of from 1 to 12 carbon atoms for the templates of formula (I) and R is an alkyl group having of from 3 to 12 carbon atoms in formula (I'). R may be a substituted or un-substituted aliphatic or cycloaliphatic group. R may be a linear or branched alkyl group, or a linear or branched alcohol. In formula (I), preferably, R contains an alkyl group of from 1 to 10 carbon atoms, more preferably from 1 to 8 carbon atoms, more preferably 1 to 6 carbon atoms, and most preferably 1 to 4 carbon atoms. Preferably R is a linear alkyl group. In formula (I'), preferably, R is a linear alkyl group having at least 3 carbon atoms, more preferably at least 4 carbon atoms.

In a more preferred embodiment, the template of formula (I) is selected from one or more of the following: N,N,N', N'-tetramethylethylenediamine, N,N,N',N'-tetramethyl-1,3-propane-diamine, N,N,N',N'-tetramethyl-1,4-butanediamine, N,N,N',N'-tetramethyl-1,3-butanediamine, N,N,N',N'-tetramethyl-1,5-pentanediamine, N,N,N',N'-tetramethyl-1,6-hexanediamine, N,N,N',N'-tetramethyl-1,7-heptanediamine, N,N,N',N'-tetramethyl-1,8-octanediamine, N,N,N',N'-tetramethyl-1,9-nonanediamine N,N,N',N'-tetramethyl-1,10-decanediamine, N,N,N',N'-tetramethyl-1,11-undecanediamine and N,N,N',N'-tetramethyl-1,12-dodecanediamine. In a most preferred embodiment the template of formula (I) is selected from N,N,N',N'-tetramethylethylenediamine and N,N,N',N'-tetramethyl-1,4-butanediamine.

In a more preferred embodiment, the template of formula (I') is selected from one or more of the following: N,N,N', N'-tetramethyl-1,3-propane-diamine, N,N,N',N'-tetramethyl-1,4-butanediamine, N,N,N',N'-tetramethyl-1,3-butanediamine, N,N,N',N'-tetramethyl-1,5-pentanediamine, N,N,N',N'-tetramethyl-1,6-hexanediamine, N,N,N',N'-tetramethyl-1,7-heptanediamine, N,N,N',N'-tetramethyl-1,8-octanediamine, N,N,N',N'-tetramethyl-1,9-nonanediamine N,N,N',N'-tetramethyl-1,10-decanediamine, N,N,N',N'-tetramethyl-1,11-undecanediamine and N,N,N', N'-tetramethyl-1,12-dodecanediamine. In a most preferred embodiment the template of formula (I') is N,N,N',N'-tetramethyl-1,4-butanediamine.

In the method of the present invention, a source of alumina, a source of phosphate and optionally a source of silica are combined with a source of fluoride and the template. Preferably, the ratio of fluorine to alumina in the reaction mixture is in the range of from 0.1 to 1.5, more preferably in the range of from 0.3 to 1.25, more preferably in the range of from 0.4 to 1.1, and even more preferably within the range of from 0.5 to 1.05. Preferably, the ratio of template to alumina is in the range of from 0.033 to 1.5, more preferably in the range of from 0.2 to 1.25, more preferably in the range of from 0.4 to 1.1, and even more preferably within the range of from 0.5 to 1.05.

The sources of aluminum, phosphorus and silicon suitable for use in the synthesis of molecular sieves according to the present invention are typically those known in the art or as described in the literature for the production of the SAPO concerned. The aluminum source may be, for example, an aluminum oxide (alumina), optionally hydrated, an aluminum salt, especially a phosphate, an aluminate, or a mixture thereof. A preferred source is a hydrated alumina, most preferably pseudoboehmite, which contains about 75% $Al_2O_3$ and 25% $H_2O$ by weight. Advantageously, the source of phosphorus is a phosphoric acid, especially orthophosphoric acid, but other sources, for example, organic phosphates, e.g., triethyl phosphate, and aluminophosphates may be used. Advantageously, the source of silicon is silica, for example colloidal silica, fumed silica, or an organic silicon source, e.g., a tetraalkyl orthosilicate, especially tetraethyl orthosilicate.

It has been found that when a template according to the present invention is used in combination with hydrogen fluoride the resulting silicoaluminophosphates have a Si/CHA cage ratio within the range of from 0.0 to 1.0. The preferred silicoaluminophosphates of the present invention have a Si/CHA cage ratio of from 0.01 to 1.0, preferably of from 0.05 to 0.50, more preferably of from 0.10 to 0.45.

In a further aspect of the present invention it has been found that the combination of organic template according to the present invention with hydrogen fluoride enables silicoaluminophosphates to be prepared in relatively short crystallization times. This may also be achieved at relatively low crystallization temperatures. The crystallizations may be completed in less than 16 hours, preferably 10 hours or less, more preferably 6 hours or less and most preferably 5 hours or less. Ideally the crystallization is undertaken at between 1 to 16 hours, preferably 1 to 10 hours, more preferably 1 to 6 hours and even more preferably 1 to 5 hours. It is preferred that the crystallization us undertaken at a temperature of less than 200° C., more preferably 175° C. or less, more preferably 160° C. or less and even more preferably at 150° C. or less. The preferred temperature ranges are from 120° C. to 200° C., more preferably from 120° C. to 175° C., even more preferably from 120° C. to 160° C. and most preferably 120° C. to 150° C. It is preferred that when the temperature is 150° C. or less and that the crystallization time is at least 2 hours.

In one preferred embodiment it is preferred that the templating agent and fluoride are substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent and remove the fluoride.

In one embodiment, the calcined silicoaluminophosphate molecular sieve has a Si/Al ratio of from 0.01 to 0.1, preferably of from 0.02 to 0.095, more preferably of from 0.02 to 0.09, and even more preferably from 0.02 to 0.085.

Method for Making Molecular Sieve Catalyst Compositions

The aluminophosphate and silicoaluminophosphate molecular sieves of the present invention may be combined with one or more formulating agents, to form a molecular sieve catalyst composition or a formulated molecular sieve catalyst composition. The formulating agents may be one or more materials selected from the group consisting of binding agents, matrix or filler materials catalytically active materials and mixtures thereof. This formulated molecular sieve catalyst composition is formed into useful shape and sized particles by well-known techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminium chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminium oxide matrix following heat treatment.

Aluminium chlorhydrol, a hydroxylated aluminium based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminium oxyhydroxide, γ-alumina, boehmite, diaspore, and transitional aluminas such as α-alumina, β-alumina, γ-alumina, δ-alumina, ε-alumina, κ-alumina, and ρ-alumina, aluminium trihydroxide, such as gibbsite, bayerite, nordstrandite, doyelite, and mixtures thereof.

In another embodiment, the binders are alumina sols, predominantly comprising aluminium oxide, optionally including some silicon. In yet another embodiment, the binders are peptised alumina made by treating alumina hydrates such as pseudobohemite, with an acid, preferably an acid that does not contain a halogen, to prepare sols or aluminium ion solutions. Non-limiting examples of commercially available colloidal alumina sols include Nalco 8676 available from Nalco Chemical Co., Naperville, Ill., and Nyacol available from The PQ Corporation, Valley Forge, Pa.

The metalloaluminophosphate molecular sieve may be combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of the following: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In one embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is clay or a clay-type composition, preferably the clay or clay-type composition having a low iron or titania content, and most preferably the matrix material is kaolin. Kaolin has been found to form a pumpable, high solid content slurry; it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In one embodiment, the binder, the molecular sieve and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, may be in the same or different liquid, and may be combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100C° C. to about 225° C. In an embodiment, the average diameter of the spray dried formed catalyst composition is from about 40 $\mu$m to about 300 $\mu$m, preferably from about 50 $\mu$m to about 250 $\mu$m, more preferably from about 50 $\mu$m to about 200 $\mu$m, and most preferably from about 65 $\mu$m to about 90 $\mu$m.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomisation fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve in powder form.

Generally, the size of the powder is controlled to some extent by the solids content of the slurry. However, control of the size of the catalyst composition and its spherical characteristics are controllable by varying the slurry feed properties and conditions of atomisation.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapour. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

In addition to the metalloaluminophosphate molecular sieve, the catalyst compositions of the present invention may comprise one or several other catalytically active materials. In one embodiment, one or several metalloaluminophosphate molecular sieves are combined with one more of the following non-limiting examples of catalytically active molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336, 478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698, 217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639, 357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236, 575), MCM-56 (U.S. Pat. No. 5,362,697), AlPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345).

In another embodiment, the metalloaluminophosphate may be bound to another molecular sieve, as disclosed for example in the following: SAPO-34 bound AlPO$_4$-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference. Binder may no longer be necessary in such systems.

In a further embodiment, the metalloaluminophosphate molecular sieve may be combined with a metal catalyst, for example as a Fischer-Tropsch catalyst.

Process for Using the Molecular Sieve Catalyst Compositions

The molecular sieve catalysts and compositions of the present invention can be employed as a catalyst in a variety of organic compound conversion processes. Examples of such processes include: cracking, hydrocracking, isomerization, polymerisation, reforming, hydrogenation, dehydrogenation, dewaxing, hydrodewaxing, absorption, alkylation, transalkylation, dealkylation, hydrodecylization, disproportionation, oligomerization, dehydrocyclization and combinations thereof.

The preferred processes of the present invention include a process directed to the conversion of a feedstock comprising one or more oxygenates to one or more olefin(s) and a process directed to the conversion of ammonia and one or more oxygenates to alkyl amines and in particular methylamines.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as gas-to-olefins (GTO) or alternatively, methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapour form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidised bed process (includes a turbulent bed process), preferably a continuous fluidised bed process, and most preferably a continuous high velocity fluidised bed process.

The reaction processes can take place in a variety of catalytic reactors such as hybrid reactors that have a dense bed or fixed bed reaction zones and/or fast fluidised bed reaction zones coupled together, circulating fluidised bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle*

Systems, pages 48 to 59, F. A. Zenz and D. F. Othmer, Reinhold Publishing Corporation, New York, 1960, and U.S. Pat. No. 6,166,282 (fast-fluidised bed reactor), and U.S. patent application Ser. No. 09/564,613 filed May 4, 2000 (multiple riser reactor), which are all herein fully incorporated by reference.

In the preferred embodiment, a fluidised bed process or high velocity fluidised bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of liquid feedstock fed separately or jointly with a vapour feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapour feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel; typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 hr$^{-1}$ to about 20,000 hr$^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa. The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidised state within a reactor.

Typically, the WHSV ranges from about 1 hr$^{-1}$ to about 5000 hr$^{-1}$, preferably from about 2$^{-1}$ hr to about 3000 hr$^{-1}$, more preferably from about 5 hr$^{-1}$ to about 1500 hr$^{-1}$, and most preferably from about 10 hr$^{-1}$ to about 1000 hr$^{-1}$. In one preferred embodiment, the WHSV is greater than 20 hr$^{-1}$; preferably the WHSV for conversion of a feedstock containing methanol and dimethyl ether is in the range of from about 20 hr$^{-1}$ to about 300 hr$^{-1}$.

The superficial gas velocity (SGV) of the feedstock including diluent and reaction products within the reactor system is preferably sufficient to fluidise the molecular sieve catalyst composition within a reaction zone in the reactor. The SGV in the process, particularly within the reactor system, more particularly within the riser reactor(s), is at least 0.1 meter per second (m/s), preferably greater than 0.5 m/s, more preferably greater than 1 m/s, even more preferably greater than 2 m/s, yet even more preferably greater than 3 m/s, and most preferably greater than 4 m/s. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 hr$^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the processes for converting an oxygenate such as methanol to one or more olefin(s) using a molecular sieve catalyst composition, the WHSV is from 0.01 hr$^{-1}$ to about 100 hr$^{-1}$, at a temperature of from about 350° C. to 550° C., and silica to Me$_2$O$_3$ (Me is a Group IIIA or VIII element from the Periodic Table of Elements) molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, preferably after passing through a catalyst cooler. In one embodiment, a carrier, such as an inert gas, feedstock vapour, steam or the like, semi-continuously or continuously, facilitates the introduction of the regenerated molecular sieve catalyst composition to the reactor system, preferably to the one or more riser reactor(s).

By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained. There are many techniques for controlling the flow of a molecular sieve catalyst composition described in Michael Louge, Experimental Techniques, Circulating Fluidised Beds, Grace, Avidan and Knowlton, eds. Blackie, 1997 (336–337), which is herein incorporated by reference.

Coke levels on the molecular sieve catalyst composition are measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one preferred embodiment, the mixture of fresh molecular sieve catalyst composition and regenerated molecular sieve catalyst composition and/or cooled regenerated molecular sieve catalyst composition contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference.

The gaseous effluent is withdrawn from the disengaging system and is passed through a recovery system. There are many well-known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

The metalloaluminophosphate molecular sieve materials and catalyst compositions of the present invention may be used in the manufacture of alkylamines, using ammonia. Examples of suitable processes are as described in published European Patent Application EP 0 993 867 A1, and in U.S. Pat. No. 6,153,798 to Hidaka et al., which are herein fully incorporated by reference.

In order to provide a better understanding of the present invention including representative advantages thereof, the following examples are offered.

EXAMPLES

XRD

X-ray Powder Diffractograms were recorded on Siemens D500 diffractometer with voltage of 40 kV and current of 30 mA, using a Cu target ($\lambda$=0.154 nm) and a graphite monochromator. Elemental analysis of Al, Si, and P was performed using the Inductively Coupled Plasma (ICP) spectroscopy.

Example 1

Preparation of aluminophosphate of framework type CHA using N,N,N',N'-tetramethylenediamine (TMED) as template in combination with HF 47.1 g $H_3PO_4$ (85% obtained from Aldrich Chemical Company), and 80 g $H_2O$ (deionized) were mixed together in a plastic beaker. To this phosphoric acid mixture was added 28.2 g Catapal A alumina (73.9 wt % $Al_2O_3$, available from CONDEA Vista Company, Texas, USA); the resulting mixture was mixed with a spatula for approximately 1 minute to form a gel which was allowed to age at room temperature for five minutes and then mixed again with a spatula for a further minute. Then to this mixed and aged gel 23.8 g of N,N,N',N'-tetramethylenediamine was added along with 8.2 g of HF (50%) and 37.7 g of deionized water. The resultant mixture was mixed with a spatula for about one minute and then thoroughly homogenized in a blender for five minutes. The mixture had the following composition:

1.0HF:1.0TMED:1.0$Al_2O_3$:1.0$P_2O_5$:40$H_2O$

The mixture was divided into eight Teflon-lined autoclaves (PARR acid digestion bombs). This mixture was reacted under different conditions for each autoclave: 3 autoclaves were heated at 160° C. in an air oven for 7.5, 24 or 48 hours, respectively; 3 other autoclaves were heated at 200° C. in an air oven for 7.5, 24 or 48 hours, respectively; and the other 2 autoclaves were heated at 135° C. for 24 and 48 hours, respectively. The solid product was recovered from each autoclave, centrifuged and washed by re-slurrying with water, centrifuging and decanting four times. The resultant product were then dried in a 115° C. The samples were analyzed by X-ray powder diffraction and found to have be $AlPO_4$-34 (CHA) having a diffraction pattern as shown in Table 1.

TABLE 1

| 2 θ | d (A) | I % |
|---|---|---|
| 9.64 | 9.172 | 100 |
| 12.43 | 7.115 | 6 |
| 13.4 | 6.602 | 5 |
| 13.52 | 6.542 | 5 |
| 13.98 | 6.331 | 18 |
| 15.29 | 5.789 | 25 |
| 16.19 | 5.469 | 27 |
| 17.88 | 4.957 | 42 |
| 19.36 | 4.582 | 4 |
| 20.10 | 4.413 | 30 |
| 20.30 | 4.372 | 40 |
| 21.36 | 4.157 | 41 |
| 22.04 | 4.030 | 48 |
| 22.29 | 3.985 | 18 |
| 22.98 | 3.868 | 7 |
| 23.65 | 3.759 | 8 |
| 24.64 | 3.610 | 18 |
| 25.05 | 3.552 | 10 |
| 25.49 | 3.492 | 27 |
| 26.37 | 3.377 | 7 |
| 26.99 | 3.301 | 2 |
| 27.28 | 3.266 | 3 |
| 28.25 | 3.156 | 3 |
| 28.95 | 3.081 | 4 |
| 29.18 | 3.058 | 10 |
| 30.32 | 2.946 | 14 |
| 30.54 | 2.925 | 33 |
| 30.90 | 2.892 | 13 |
| 31.33 | 2.853 | 5 |
| 31.63 | 2.826 | 11 |
| 32.01 | 2.794 | 1 |
| 32.80 | 2.728 | 26 |
| 32.99 | 2.713 | 37 |
| 33.21 | 2.696 | 37 |
| 34.50 | 2.598 | 8 |
| 34.69 | 2.583 | 8 |
| 34.94 | 2.566 | 12 |
| 36.06 | 2.488 | 3 |
| 36.40 | 2.466 | 3 |
| 36.91 | 2.433 | 2 |
| 38.94 | 2.311 | 4 |
| 39.35 | 2.288 | 5 |

A portion of the sample that was heated at 200° C. for 24 hours was calcined in air at 650° C. to remove the template and fluoride. The sample was then mounted inside a high temperature X-ray diffraction cell and the temperature of the sample was maintained at 170° C. under a flow of dry nitrogen. The X-ray diffraction pattern is given in Table 2 and demonstrated that this sample is an aluminophosphate of rhombohedral CHA framework type.

TABLE 2

| 2 θ | d (A) | I % |
|---|---|---|
| 9.53 | 9.273 | 100 |
| 12.93 | 6.840 | 46 |
| 14.03 | 6.305 | 7 |
| 16.06 | 5.513 | 22 |
| 17.85 | 4.964 | 29 |
| 19.13 | 4.635 | 4 |
| 20.69 | 4.290 | 53 |
| 22.11 | 4.017 | 1 |
| 22.4 | 3.949 | 1 |
| 23.16 | 3.837 | 3 |
| 25.06 | 3.551 | 18 |

TABLE 2-continued

| 2 θ | d (A) | I % |
|---|---|---|
| 26.02 | 3.422 | 15 |
| 27.77 | 3.210 | 3 |
| 28.28 | 3.153 | 2 |
| 29.71 | 3.005 | 1 |
| 30.75 | 2.905 | 34 |
| 30.91 | 2.890 | 36 |
| 31.20 | 2.865 | 17 |
| 31.74 | 2.817 | 1 |
| 32.49 | 2.753 | 1 |
| 33.51 | 2.672 | 2 |
| 33.66 | 2.660 | 2 |
| 34.63 | 2.588 | 6 |
| 35.13 | 2.552 | 1 |
| 36.17 | 2.481 | 5 |
| 38.80 | 2.319 | 1 |

Example 2

Preparation of aluminophosphate of framework type CHA using N,N,N',N'-tetramethyl-1,4-butanediamine (TMBD) as template in combination with HF 24.5 g $H_3PO_4$ (85% obtained from Aldrich Chemical Company), and 40 g $H_2O$ (deionized) were mixed together in a plastic beaker. To this phosphoric acid mixture was added 14.7 g Catapal A alumina (73.9 wt % $Al_2O_3$, available from CONDEA Vista Company, Texas, USA); the resulting mixture was mixed with a spatula for approximately 1 minute to form a gel which was allowed to age at room temperature for five minutes and then mixed again with a spatula for a further minute. Then to this mixed and aged gel 15.3 g of N,N,N',N'-tetramethyl-1,4-butanediamine was added along with 4.3 g of HF (50%) and 21.2 g of deionized water. The resultant mixture was mixed with a spatula for about one minute and then thoroughly homogenized in a blender for ten minutes. The mixture had the following composition:

1.0 HF:1.0TMBD:1.0$Al_2O_3$:1.0$P_2O_5$:40$H_2O$

The mixture was divided into eight Teflon-lined autoclaves (PARR acid digestion bombs). Each autoclave was heated under different conditions: the first three were heated at 160° C. for 6.5, 24 or 48 hours, respectively, three others were heated at 200° C., for 6.5, 24 or 48 hours, respectively, and the last two were heated at 135° C. for 24 or 48 hours, respectively. The solid product was recovered from each autoclave, centrifuged and washed by re-slurrying with water, centrifuging and decanting four times. The resultant products were then dried in a 115° C. The samples were analyzed by X-ray powder diffraction and found to have be $AlPO_4$-34 (CHA) having a diffraction pattern similar to that shown in Table 1.

Example 3

Preparation of silicoaluminophosphate of framework type CHA using N,N,N',N'-tetramethylethylenediamine (TMED) as template in combination with HF.

Eight mixtures of 18.9 g $H_3PO_4$ (85% obtained from Aldrich Chemical Company), 32.5 g $H_2O$ (deionized), 1.6 g of HF (50%), 1.2 g of colloidal silica (40% $SiO_2$ DuPont Ludox, AS40) 9.5 g of N,N,N',N'-tetramethylethylenediamine and 11.3 g Catapal A alumina (73.9 wt % $Al_2O_3$, available from CONDEA Vista Company, Texas, USA), were prepared and each mixture was placed in a 125 ml Teflon-lined autoclave (PARR 4748 acid digestion bomb). Each of the eight mixtures had the following composition:

0.5HF:1.0TMED:1.0$Al_2O_3$:1.0$P_2O_5$:0.1$SiO_2$:30$H_2O$.

Each of the eight mixtures was mixed for about one minutes with a Teflon stir bar and then mounted in a rotating shelf (~20 rpm) in preheated ovens at different temperatures and for different periods of time: the first four were heated at 120° C. for 2, 4, 6 or 8 hours, respectively; the other four were heated at 150° C. for 2, 4, 6 or 8 hours, respectively. The solid products were recovered from each autoclave, centrifuged and washed by re-slurrying with water, centrifuging and decanting four times. The resultant products were then dried in a 115° C. The samples were analyzed by X-ray powder diffraction which showed that, except for the product heated for 2 hours at 120° C., all other seven samples were fully crystalline SAPO-34 (CHA) having a diffraction pattern similar to that shown in Table 1.

Elemental analysis by ICP-AES gave the following results for the product obtained after 2 hr/150° C.: Al, 16.6%; Si, 0.811%; P, 18.5%; which corresponds to the following composition: $Al_{0.496}Si_{0.023}P_{0.481}O_2$ and for the product obtained after 4 hr/120° C.: Al, 16.8%; Si, 0.751%; P, 18.9%; which corresponds to the following composition: $Al_{0.494}Si_{0.021}P_{0.485}$. A portion of the material obtained after 2 hr/150° C. was calcined in air for two hours at 650° C. and three hours at 650° C. to remove the template and the fluoride ion. The sample was then evacuated overnight at 400° C. on an automated CAHN vacuum microbalance absorption unit to less than $1\times10^{-4}$ torr pressure. After cooling to room temperature the sample absorbed 25% methanol at 41 torr at 24° C.

This example illustrates that aluminophosphate molecular sieve of CHA framework type may be prepared in less than two hours using the organic templates according to the present invention in combination with hydrogen fluoride.

Example 4

Preparation of silicoaluminophosphate of framework type CHA using N,N,N',N'-tetramethylethylenediamine (TMED) as template in combination with HF 18.6 g $H_3PO_4$ (85% obtained from Aldrich Chemical Company) and 20 g $H_2O$ (deionized), were mixed in a plastic beaker. To this phosphoric acid mixture was added 11.1 g Catapal A alumina (73.9 wt % $Al_2O_3$, available from CONDEA Vista Company, Texas, USA), with mixing with a spatula for approximately one minute. The resulting gel was allowed to age for about five minutes at room temperature and was then mixed for a further one minute with a spatula. Then a solution of 9.4 g of N,N,N',N'-tetramethylethylenediamine and 1.7 g of tetraethylorthosilicate (Aldrich) was added along with 1.6 g of HF (50%), and 12.7 g of deionized water. This mixture was mixed for about one minute with a spatula and was then thoroughly homogenized with a blender for five minutes. The mixture had the following composition:

0.5F:1.0 TMED:1.0$Al_2O_3$:1.0$P_2O_5$:0.1$SiO_2$:30$H_2O$.

The mixture was placed in a 125 ml Teflon-lined autoclave (PARR 4748 acid digestion bomb) and then mounted in a rotating shelf (~20 rpm) in preheated 150° C. oven for 4.5 hours. The solid product was recovered from the autoclave centrifuged and washed by re-slurrying with water, centrifuging and decanting four times. The resultant product was then dried in a 115° C. The sample was analyzed by X-ray powder diffraction, which showed that the product was a SAPO-34 (CHA) having a diffraction pattern similar to that shown in Table 1. Elemental analysis by ICP-AES gave the following results for the product: Al, 17.3%; Si, 0.583%; P, 19.2%; which corresponds to the following composition: $Al_{0.500}Si_{0.016}P_{0.484}O_2$.

Example 5

Methanol-to Olefins Performance

The product of Example 4 was evaluated for performance in the methanol to olefins reaction. This sample was activated in air at 650° C. for three hours to remove the template and fluoride. The activated material was pelletized, crushed and sieved to 80–120 mesh size. The silicoaluminophosphate was then diluted with quartz and loaded into a fixed bed reactor. A methanol feedstock was metered into the reactor at a feed rate of 0.051 ml/minute. The pressure of the reactor was maintained at 25 psig. The methanol was passed across the catalyst bed at 475° C. and a WHSV (weight hour space velocity) of 151. The reactor effluent was passed to an on-line gas chromatograph. Weight averaged selectivity was calculated for key components until conversion fell below 10%. Yields were calculated on a water-free basis, but conversion is based on methanol/DME including water. Catalyst life is determined as the amount of methanol converted per gram of sieve until conversion falls below 10%. The results are provided in Table 3.

TABLE 3

| SAPO | Wt Average Selectivity ($C_2$= + $C_3$=) | Wt Average Selectivity Propane | Catalyst Life GMEOHconv./gcat | Ratio $C_2$=/$C_3$= | Wt Average Selectivity $C_4$+ |
|---|---|---|---|---|---|
| Ex. 4 | 70.3 | 0.7 | 14.4 | 0.77 | 20.1 |

The data in table 3 shows that the sample of example 4 has good MTO performance and in particular has low propane selectivity.

What is claimed is:

1. A process for preparing microporous crystalline silicoaluminophosphate molecular sieves of CHA framework type, the process comprising:
    (a) providing a reaction mixture comprising a source of alumina, a source of phosphate, a source of silica, hydrogen fluoride and an organic template comprising one or more compounds of formula (I):

$(CH_3)_2N-R-N(CH_3)_2$    (I)

wherein R is an alkyl radical of from 1 to 12 carbon atoms;
    (b) inducing crystallization of silicoaluminophosphate from the reaction mixture; and
    (c) recovering silicoaluminophosphate molecular sieve.
2. The process of claim 1, further comprising the step of (d) calcining the molecular sieve obtained in step (c).
3. The process of claim 1, wherein R is a linear alkyl group.
4. The process of claim 1, wherein R has from 1 to 10 carbon atoms.
5. The process of claim 4, wherein R has from 1 to 8 carbon atoms.
6. The process of claim 4, wherein R has from 1 to 6 carbon atoms.
7. The process of claim 4, wherein R has from 1 to 4 carbon atoms.
8. The process of claim 1, wherein the template is selected from one or more of the group consisting of: N,N,N',N'-tetramethyl ethylenediamine, N,N,N',N'-tetramethyl-1,3-propane-diamine, N,N,N',N'-tetramethyl-1,4-butanediamine, N,N,N',N'-tetramethyl-1,3-butanediamine, N,N,N',N'-tetramethyl-1,5-pentanediamine, N,N,N',N'-tetramethyl-1,6-hexanediamine, N,N,N',N'-tetramethyl-1,7-heptanediamine, N,N,N',N'-tetramethyl-1,8-octanediamine, N,N,N',N'-tetramethyl-1,9-nonanediamine N,N,N',N'-tetramethyl-1,10-decanediamine, N,N,N',N'-tetramethyl-1,11-undecanediamine and N,N,N',N'-tetramethyl-1,12-dodecanediamine.
9. The process of claim 8, wherein the template is selected from N,N,N',N'-tetramethyl ethylenediamine and N,N,N',N'-tetramethyl-1,4-butanediamine.
10. The process of claim 1, wherein crystallization takes place for a period of time of from 1 to 16 hours.
11. The process of claim 10, wherein crystallization takes place for a period of from 1 to 10 hours.
12. The process of claim 10, wherein crystallization takes place for a period of from 1 to 5 hours.
13. The process of claim 1, wherein crystallization takes place at a temperature of 175° C. or less.
14. A process for preparing microporous crystalline aluminophosphate molecular sieves of CHA framework type, the process comprising:
    (a) providing a reaction mixture comprising a source of alumina, a source of phosphate, hydrogen fluoride and an organic template comprising one or more compounds of formula (I'):

$(CH_3)_2N-R-N(CH_3)_2$    (I')

wherein R is an alkyl radical of from 3 to 12 carbon atoms;
    (b) inducing crystallization of aluminophosphate from the reaction mixture; and
    (c) recovering aluminophosphate molecular sieve.
15. The process of claim 14, further comprising the step of (d) calcining the molecular sieve obtained in step (c).
16. The process of claim 14, wherein R is a linear alkyl group.
17. The process of claim 14, wherein R has from 3 to 10 carbon atoms.
18. The process of claim 17, wherein R has from 3 to 8 carbon atoms.
19. The process of claim 17, wherein R has from 3 to 6 carbon atoms.
20. The process of claim 17, wherein R has from 3 to 4 carbon atoms.
21. The process of claim 14, wherein the template is selected from one or more of the group consisting of: N,N,N',N'-tetramethyl-1,3-propane-diamine, N,N,N',N'-tetramethyl-1,4-butanediamine, N,N,N',N'-tetramethyl-1,3-butanediamine, N,N,N',N'-tetramethyl-1,5-pentanediamine, N,N,N',N'-tetramethyl-1,6-hexanediamine, N,N,N',N'-tetramethyl-1,7-heptanediamine, N,N,N',N'-tetramethyl-1,8-octanediamine, N,N,N',N'-tetramethyl-1,9-nonanediamine N,N,N',N'-tetramethyl-1,10-decanediamine, N,N,N',N'-tetramethyl-1,11-undecanediamine and N,N,N',N'-tetramethyl-1,12-dodecanediamine.
22. The process of claim 21, wherein the template is N,N,N',N'-tetramethyl-1,4-butanediamine.
23. The process as claimed in claim 14, wherein crystallization takes place for a period of time of from 1 to 16 hours.

24. The process of claim 23, wherein crystallization takes place for a period of from 1 to 10 hours.

25. The process of claim 23, wherein crystallization takes place for a period of from 1 to 5 hours.

26. The process of claim 14, wherein crystallization takes place at a temperature of 175° C. or less.

27. A silicoaluminophosphate molecular sieve, substantially of framework type CHA, comprising within its intra-crystalline structure a template of formula (I).

28. The silicoaluminophosphate molecular sieve of claim 27, wherein the template of formula I is selected from one or more of the group consisting of N,N,N',N'-tetramethyl ethylenediamine, N,N,N',N'-tetramethyl-1,3-propane diamine, N,N,N',N'-tetramethyl-1,4-butanediamine, N,N,N',N'-tetramethyl-1,3-butanediamine, N,N,N',N'-tetramethyl-1,5-pentanediamine, N,N,N',N'-tetramethyl-1,6-hexanediamine, N,N,N',N'-tetramethyl-1,7-heptanediamine, N,N,N',N'-tetramethyl-1,8-octanediamine, N,N,N',N'-tetramethyl-1,9-nonanediamine N,N,N',N'-tetramethyl-1,10-decanediamine, N,N,N',N'-tetramethyl-1,11-undecanediamine and N,N,N',N'-tetramethyl-1,12-dodecanediamine.

29. The silicoaluminophosphate molecular sieve of claim 28, wherein the template is selected from N,N,N',N'-tetramethyl ethylenediamine and N,N,N',N'-tetramethyl-1,4-butanediamine.

30. The silicoaluminophosphate of claim 27, further comprising fluoride within its intra-crystalline structure.

31. The silicoaluminophosphate molecular sieve of claim 30, wherein the template is N,N,N',N'-tetramethylethylenediamine.

32. An aluminophosphate or silicoaluminophosphate molecular sieve, substantially of framework type CHA, comprising within its intra-crystalline structure N,N,N',N'-tetramethyl-1,4-butanediamine.

33. The aluminophosphate or silicoaluminophosphate molecular sieve of claim 32, further comprising fluoride within its intra-crystalline structure.

34. A process for forming a catalyst composition, the process comprising forming a mixture comprising at least one molecular sieve as claimed in claim 27 and at least one formulating agent.

35. The process of claim 34, wherein the formulating agent comprises one or more materials selected from the group consisting of binding agents, matrix or filler materials and mixtures thereof.

36. The process of claim 34, wherein the molecular sieve has a Si/Al ratio of from 0.01 to 0.1.

37. The process of claim 34, wherein the molecular sieve has a Si/Al ratio of from 0.02 to 0.095.

38. The process of claim 34, wherein the molecular sieve has a Si/Al ratio of from 0.02 to 0.09.

39. The process of claim 34, wherein the molecular sieve has a Si/Al ratio of from 0.02 to 0.085.

40. A formulated molecular sieve composition comprising at least one molecular sieve as claimed in claim 27, in admixture with at least one formulating agent.

41. The formulated molecular sieve composition of claim 40, wherein the formulating agent is one or more materials selected from the group consisting of binding agents, matrix or filler materials, and mixtures thereof.

42. The formulated molecular sieve composition of claim 40, wherein the molecular sieve has a Si/Al ratio of from 0.01 to 0.1.

43. The formulated molecular sieve composition of claim 40, wherein the molecular sieve has a Si/Al ratio of from 0.02 to 0.095.

44. The formulated molecular sieve composition of claim 40, wherein the molecular sieve has a Si/Al ratio of from 0.02 to 0.09.

45. The formulated molecular sieve composition of claim 40, wherein the molecular sieve has a Si/Al ratio of from 0.02 to 0.085.

46. A process for converting a feedstock comprising organic compounds to conversion product which comprises contacting said feedstock with a catalyst comprising an active form of the microporous crystalline silicoaluminophosphate molecular sieves prepared by the process of claim 1.

47. The process of claim 46, wherein said feedstock comprises oxygenates and said conversion product comprises one or more olefins.

\* \* \* \* \*